US008454494B2

(12) United States Patent
Timm et al.

(10) Patent No.: US 8,454,494 B2
(45) Date of Patent: Jun. 4, 2013

(54) SUPPORT APPARATUS FOR GASTRIC BAND SYSTEM INJECTOR

(75) Inventors: Richard W. Timm, Cincinnati, OH (US); Scott A. Woodruff, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 646 days.

(21) Appl. No.: 12/637,095

(22) Filed: Dec. 14, 2009

(65) Prior Publication Data
US 2011/0144419 A1    Jun. 16, 2011

(51) Int. Cl.
*A61F 2/04*    (2006.01)
(52) U.S. Cl.
USPC .......................................................... 600/37
(58) Field of Classification Search
USPC ............................ 604/187, 523, 533; 600/37
See application file for complete search history.

(56) References Cited

U.S. PATENT DOCUMENTS

| | | | | |
|---|---|---|---|---|
| 2,485,842 A * | 10/1949 | Pennington | | 604/186 |
| 5,688,244 A * | 11/1997 | Lang | | 604/118 |
| 5,704,912 A * | 1/1998 | Lawrence et al. | | 604/97.02 |
| 6,067,991 A | 5/2000 | Forsell | | |
| 6,419,643 B1 * | 7/2002 | Shimada et al. | | 600/585 |
| 6,461,292 B1 | 10/2002 | Forsell | | |
| 6,470,892 B1 | 10/2002 | Forsell | | |
| 6,652,565 B1 * | 11/2003 | Shimada et al. | | 607/105 |
| 6,855,115 B2 | 2/2005 | Fonseca et al. | | |
| 7,416,528 B2 | 8/2008 | Crawford et al. | | |
| 7,442,165 B2 | 10/2008 | Forsell | | |
| 7,621,863 B2 | 11/2009 | Forsell | | |
| 2001/0047151 A1 | 11/2001 | Xian et al. | | |
| 2003/0073061 A1 * | 4/2003 | Toomey | | 434/273 |
| 2005/0283118 A1 | 12/2005 | Uth et al. | | |
| 2006/0211914 A1 * | 9/2006 | Hassler et al. | | 600/37 |
| 2007/0235083 A1 * | 10/2007 | Dlugos | | 137/223 |
| 2008/0250340 A1 | 10/2008 | Dlugos, Jr. et al. | | |

FOREIGN PATENT DOCUMENTS

| | | |
|---|---|---|
| FR | 2 639 234 | 5/1990 |
| GB | 1476776 | * 12/1974 |
| GB | 1 476 776 | 6/1977 |

OTHER PUBLICATIONS

International Search Report dated Apr. 28, 2011 for Application No. PCT/US2010/059125.

* cited by examiner

*Primary Examiner* — Kevin C Sirmons
*Assistant Examiner* — Michael J Anderson
(74) *Attorney, Agent, or Firm* — Frost Brown Todd LLC

(57) ABSTRACT

A support apparatus connects with and provides fluid communication between a needle and a syringe. The support apparatus includes at least one arm that is configured to provide cantilever support of the needle and syringe while the needle is inserted in a patient. The arm engages the patient's skin, and may be rigid, malleable, hinged, stretchable, telescoping, and/or have other properties. The support apparatus may form part of an adapter that also includes a pressure sensor. The pressure sensor senses the pressure of fluid in a gastric band system when the needle is inserted in an injection port of the gastric band system. A cable may extend from the pressure sensor to a display device, and may include markings configured to provide measurement from the needle to a patient's xyphoid process. Such a measurement may be factored into a calculation to account for hydrostatic pressure differences in pressure readings.

19 Claims, 12 Drawing Sheets

SUPPORT APPARATUS FOR GASTRIC BAND SYSTEM INJECTOR

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Another example of such an adjustable gastric band is disclosed in U.S. Pat. No. 6,067,991, entitled "Mechanical Food Intake Restriction Device," issued May 30, 2000, the disclosure of which is incorporated by reference herein.

To the extent that an adjustable gastric band system includes an injection port configured to receive the needle of a syringe assembly to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled "System and Method for Determining Implanted Device Positioning and Obtaining Pressure Data" published Sep. 21, 2006, and issued Aug. 17, 2010 as U.S. Pat. No. 7,775,215, the disclosure of which is incorporated by reference herein.

While a variety of gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
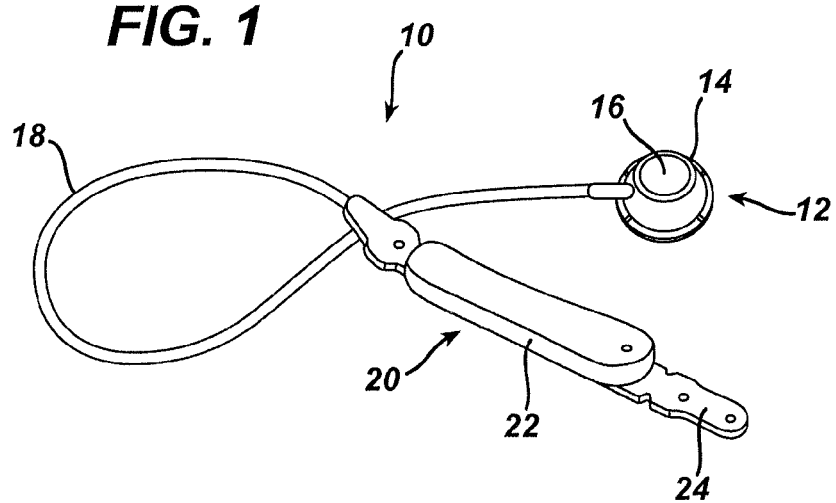
FIG. 1 depicts a perspective view of an implantable portion of an exemplary gastric band system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

FIGS. 1-4 illustrate an exemplary gastric band system (10). As shown, gastric band system (10) comprises an injection port (12), a gastric band (20), and a catheter (18). Injection port (12) of the present example comprises a port housing (14) and a needle penetrable septum (16). Port housing (14) defines a fluid reservoir (not shown), such that a needle may pierce septum (16) to reach the reservoir and add or withdraw fluid (e.g., saline, etc.) as described in greater detail below. Port housing (14) may be formed of titanium, plastic, or any other suitable material or combination of materials. Septum (16) may be formed of silicone or any other suitable material or combination of materials. Injection port (12) may be subcutaneously secured over a patient's sternum, to the patient's abdominal fascia, or in any other suitable location. In some versions, injection port (12) is configured and operable in accordance with the teachings of U.S. Pub. No. 2005/0283118, and issued Dec. 14, 2010 as U.S. Pat. No. 7,850,660, entitled "Implantable Medical Device with Simultaneous Attachment Mechanism and Method," published Dec. 22, 2005, the disclosure of which is incorporated by reference herein. Alternatively, injection port (12) may have any other suitable configuration and/or operability.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). Accordingly, a needle that is inserted through septum (16) may be used to add or withdraw fluid from inflatable bladder (22), to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
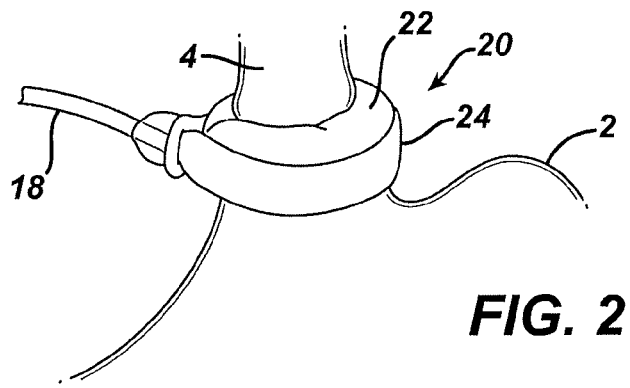
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastro-esophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
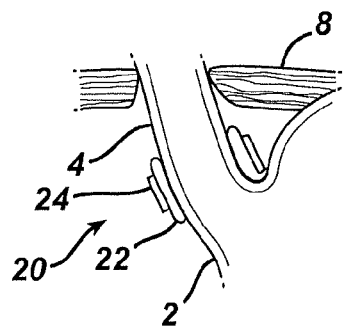
FIG. 3 depicts a cross-sectional view of the gastric band of FIG. 1, showing the band positioned around the gastro-esophageal junction of a patient in a deflated configuration.
Figure 4:
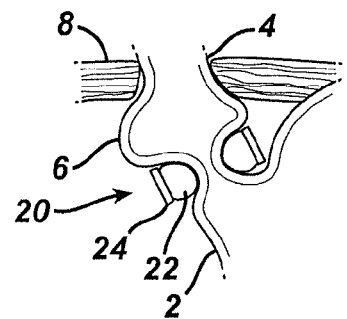
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

Figure 5:
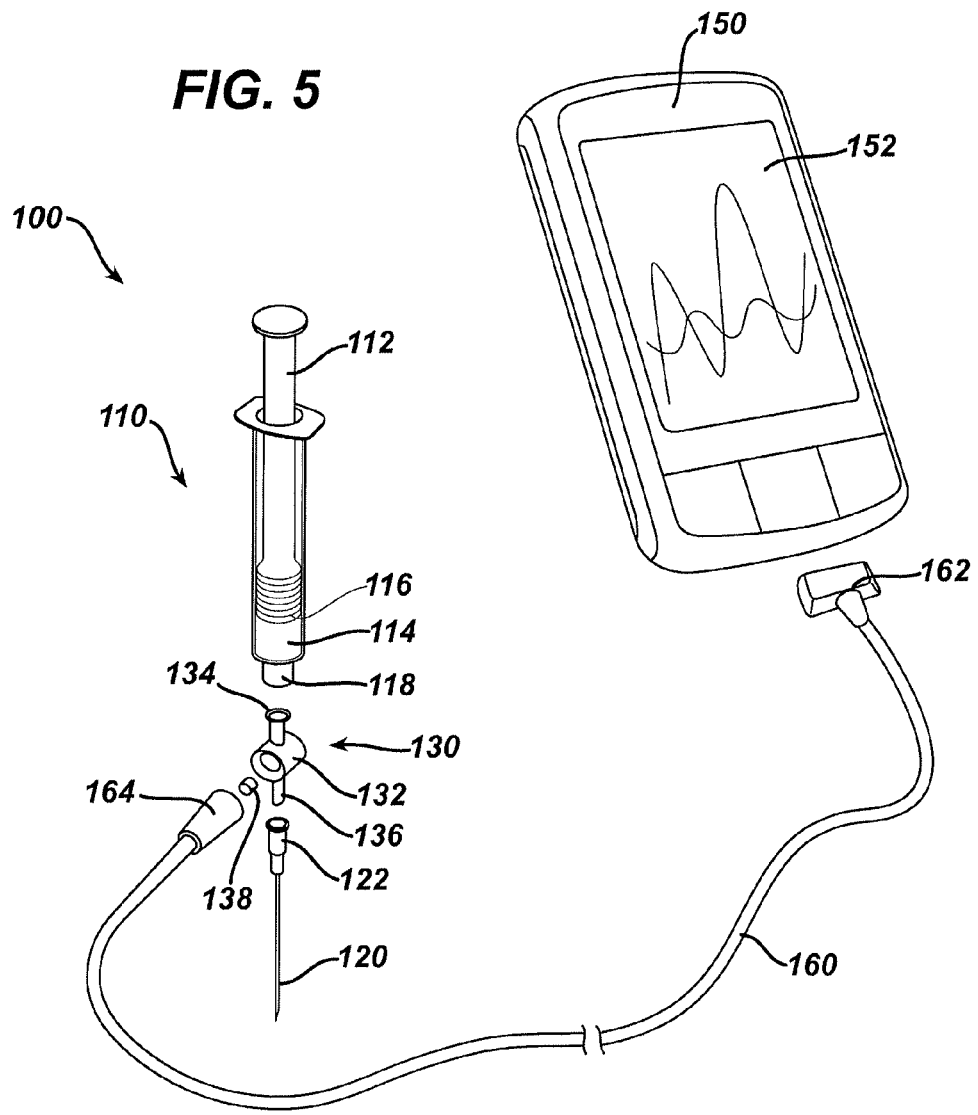
FIG. 5 depicts a perspective exploded view of an exemplary pressure sensing syringe system usable with the gastric band system of FIG. 1.

FIG. 5 shows an exemplary needle system (100) that may be used with gastric band system (10). In this example, needle system (100) comprises a syringe (110) and a display device (150) in communication via a cable (160). Syringe (110) comprises a plunger (112), a barrel (114), a pressure sensing component (130), and a needle (120). Plunger (112) includes a piston (116) that sealingly engages barrel (114). Barrel (114) includes a conventional luer lock portion (118) that is in fluid communication with the interior of barrel (114). Needle (120) comprises a conventional non-coring Huber needle, and includes a conventional luer lock portion (122). Of course, any of these components, among others, may be varied in any suitable fashion.

Pressure sensing component (130) of the present example comprises a housing that includes a body portion (132), an upper luer lock portion (134), a lower luer lock portion (136), and a pressure sensor (138). Upper luer lock portion (134) is configured to couple with luer lock portion (118) of syringe (110). Lower luer lock portion (136) is configured to couple with luer lock portion (122) of needle (120). It should therefore be understood that pressure sensing component (130) of the present example may be retrofitted to a variety of types of syringes and needles, etc. Body portion (132) provides communication of fluid between syringe (110) and needle (120). In addition, pressure sensor (138) is in fluid communication with the interior of body portion (132), such that pressure sensor (138) is operable to sense the pressure of fluid in syringe (110) and needle (120) as will be described in greater detail below. In some versions, pressure sensor (138) comprises a pressure sensor provided by CardioMEMS, Inc. of Atlanta, GA., though any other suitable type of pressure sensor may be obtained from any other suitable source. By way of example only, pressure sensor (138) may be constructed in accordance with the teachings of U.S. Pat. No. 6,855,115, entitled "Implantable Wireless Sensor for Pressure Measurement within the Heart," issued Feb. 15, 2005, the disclosure of which is incorporated by reference herein. As another merely illustrative example, pressure sensor (138) may be constructed in accordance with the teachings of U.S. Pub. No. 2006/0211914, entitled "System and Method for Determining Implanted Device Positioning and Obtaining Pressure Data," published Sep. 21, 2006, and issued Aug. 17, 2010 as U.S. Pat. No. 7,775,215, the disclosure of which is incorporated by reference herein. Still other suitable forms of pressure sensor (138) may take will be apparent to those of ordinary skill in the art in view of the teachings herein.

Cable (160) of the present example has a boot portion (164), which is configured to selectively attach to pressure sensing component (130). Boot portion (164) includes a feature (not shown) that is operable to electrically engage with pressure sensor (138) and thereby communicate pressure readings obtained by pressure sensor (138) along cable (160). Such a feature may comprise one or more terminals (not shown) or any other suitable type(s) of feature(s) as will be apparent to those of ordinary skill in the art. In the present example, boot portion (164) is removably coupled with pressure sensing component (130), though it should be understood that such a coupling may be substantially permanent or integral, etc. The other end of cable (160) includes a connector (162) that couples with display device (150). Cable (160) is thereby operable to communicate data obtained by pressure sensor (138) to display device (150). Display device (150) is operable to process such data and render feedback to the user via display (152).

In some versions, display device (150) comprises a dedicated device constructed for the purpose of processing pressure data and providing graphical and/or textual output to the user via display (152). In some other versions, display device (150) comprises a conventional portable electronic device (e.g., a BlackBerry, an iPhone, a laptop computer, etc.) with software that is operable to process pressure data and provide graphical and/or textual output to the user. In still other versions, display device (150) comprises a desktop PC or other type of computer with software that is operable to process pressure data and provide graphical and/or textual output to the user. Still various other forms that display device (150) may take will be apparent to those of ordinary skill in the art in view of the teachings herein. It should also be understood that cable (160) may comprise a conventional USB cable or some other type of cable. Furthermore, cable (160) may be omitted in some versions, such as versions where pressure sensing component (130) is operable to communicate to display device (150) wirelessly. Examples of such wireless communication are disclosed in U.S. Pub. No. 2006/0211914, entitled "System and Method for Determining Implanted Device Positioning and Obtaining Pressure Data," published Sep. 21, 2006, and issued Aug. 17, 2010 as U.S. Pat. No. 7,775,215, the disclosure of which is incorporated by reference herein; while other examples of wireless communication will be apparent to those of ordinary skill in the art in view of the teachings herein.

In one merely exemplary use, where gastric band system (10) has been implanted in a patient, needle (120) is inserted into a patient at an injection point to reach septum (16) of injection port (12). Upon such insertion, needle (120) is in fluid communication with gastric band system (10), such that the pressure of the fluid in gastric band system (10) and needle system (100) will be substantially equalized. It will therefore be appreciated that fluid pressure sensed by pressure sensor (138) may be indicative of the pressure of fluid within gastric band system (10). In some settings, such pressure information may be useful during a process of using needle system (100) to adjust fluid pressure of gastric band system (10) by adding or withdrawing fluid to or from gastric band system (10). In particular, the configuration of syringe (110) and pressure sensing component (130) may permit substantially simultaneous adjustment and reading of fluid pressure.

For instance, a user may first insert needle (120) into the patient to reach septum (16) of injection port (12). Upon pressure equalization, the user may then read the initial pressure via display device (150). It will be understood that pressure equalization may be determined by a pressure reading remaining substantially constant. The user may then add or withdraw fluid to or from gastric band system (10) using syringe; by pushing plunger (112) further into barrel (114) or withdrawing plunger (112) further from barrel (114), respectively. The user may monitor display device (150) during such adding/withdrawing of fluid to monitor the fluid pressure in substantially real time. To the extent that there is a delay between the user's manipulation of syringe (110) and the time the pressure substantially equalizes among syringe (110) and gastric band system (10), the user may simply wait until the pressure reading indicated through display device (150) becomes substantially constant. Still other suitable ways in which needle system (100) may be used in conjunction with a gastric band system (10) will be apparent to those of ordinary skill in the art in view of the teachings herein.

Pressure data obtained using pressure sensing component (130) may need to be adjusted in order to provide an accurate indication of the pressure in gastric band (20). Specifically, there may be a hydrostatic pressure difference between the pressures at gastric band (20) and at port (12) because port (12) is located at a different height than gastric band (20), particularly if the patient is sitting up or standing up. In order to account for the pressure difference, a user may need to determine the height difference between port (12) and gastric band (20). This may be accomplished by measuring the height difference between pressure sensing component (130), which is approximately the same height as port (12) in the present example, and the patient's xyphoid process ("xyphoid"), which is approximately the same height as gastric band (20) in the present example. The xyphoid is a small bony extension to the sternum below the gladiolus and the manubrium. Once the height difference is measured, then the user, or properly configured software, may use the height difference and an appropriate formula (e.g., the static form of Bernoulli's Equation, $\Delta p = \rho g h$) to adjust the pressure data obtained by pressure sensing component (130) to account for the hydrostatic pressure difference. In this equation, $\Delta p$ represents the pressure difference of interest, $\rho$ is the density of the fluid (e.g., saline), g is the gravitational acceleration constant, and h is the height different from pressure sensing component (130) to the patient's xyphoid (which may be representative of the height of gastric band (20).

Figure 6:
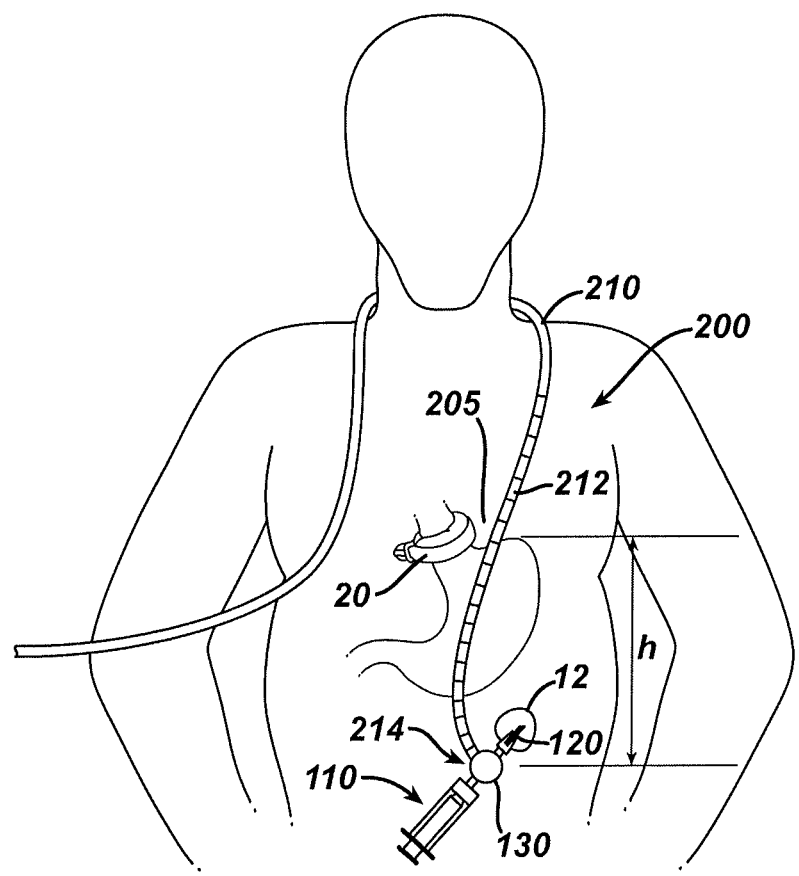
FIG. 6 depicts a front view of a patient and an exemplary measurement device.
Figure 7:
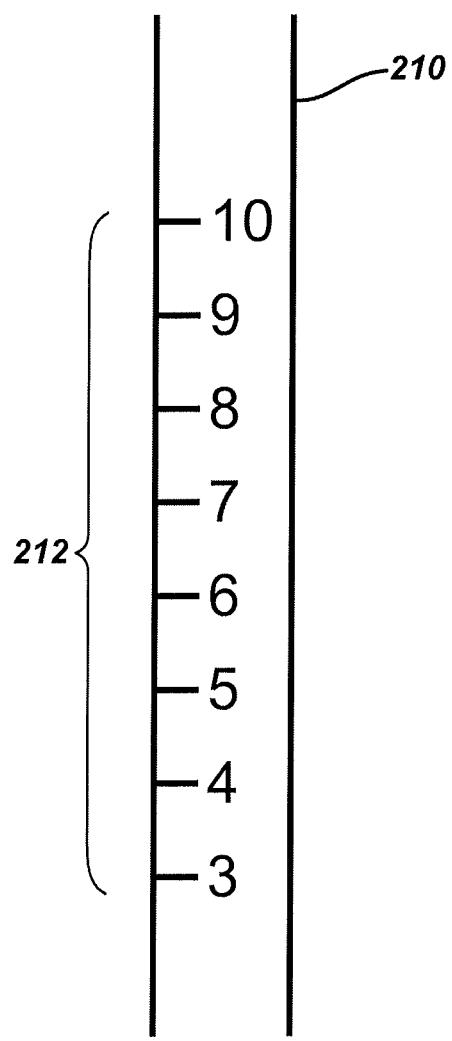
FIG. 7 depicts a detailed, front view of exemplary markings on the cable of the measurement device of FIG. 6.

FIGS. 6-7 depict an example of a measurement device (200) configured to facilitate measurement of the distance (h) between pressure sensing component (130) and the patient's xyphoid (205). In this example, measurement device (200) comprises a cable (210) that incorporates a plurality of equally spaced markings (212) that may be used to indicate distance. FIG. 7 depicts a close-up view of one example of markings (212). Any suitable number of markings (212) may be used, and the markings may represent any suitable unit of measurement, including but not limited to millimeters, centimeters, and inches. Markings (212) may have varying characteristics, such as length or width, to denote fractions of a specific unit of measurement, although this is not required. Markings (212) may be made on or in cable (210) using any suitable method, including but not limited to attaching one or more stickers, printing, etching, molding, laser marking, etc. Cable (210) may be selectively engaged with pressure sensing component (130) at a first end (214). Cable (210) may include a boot portion (not shown), similar to the above-described boot portion (164), configured to couple cable (210) and pressure sensing component (130). Cable (210) may be selectively engaged with a display/processing unit, including but not limited to the above-described display device (150), at a second end (not shown). For instance, cable (210) may include a connector (not shown) similar to connector (162) configured to couple cable (210) and a display device. Similar to cable (160) described above, cable (210) may be operable to communicate data obtained by pressure sensor (138) to a display device, although this is not required. Cable (210) may comprise a conventional USB cable or some other type of cable. Thus, cable (210) may be essentially identical to cable (160) described above, except that cable (210) includes markings (212).

As shown in FIG. 6, cable (210) extends vertically from pressure sensing component (130) along the patient's torso, around the patient's neck, and subsequently extends toward a display device (not shown). In the illustrated configuration, cable (210), specifically the portion of cable (210) containing markings (212), is aligned to measure the height difference between pressure sensing portion (130) and the patient's xyphoid (205). In addition, in this version, cable (210) is also configured to support at least a portion of the weight of syringe (110), which may reduce patient discomfort and/or performance issues related to syringe (110) being unsupported when the patient is in a sitting or standing position. Other suitable configurations and orientations where markings (212) on cable (210) are substantially aligned with the distance between pressure sensing component (130) and xyphoid (205) and/or where cable (210) supports at least a portion of the weight of syringe (110) will be apparent to those skilled in the art in view of the teachings herein. Similarly, other suitable variations of cable (210), including but not limited to alternative functionalities, features, components, structures, configurations, substitutes, and supplements for cable (210), will be apparent to those of ordinary skill in the art in view of the teachings herein.

Figure 8:
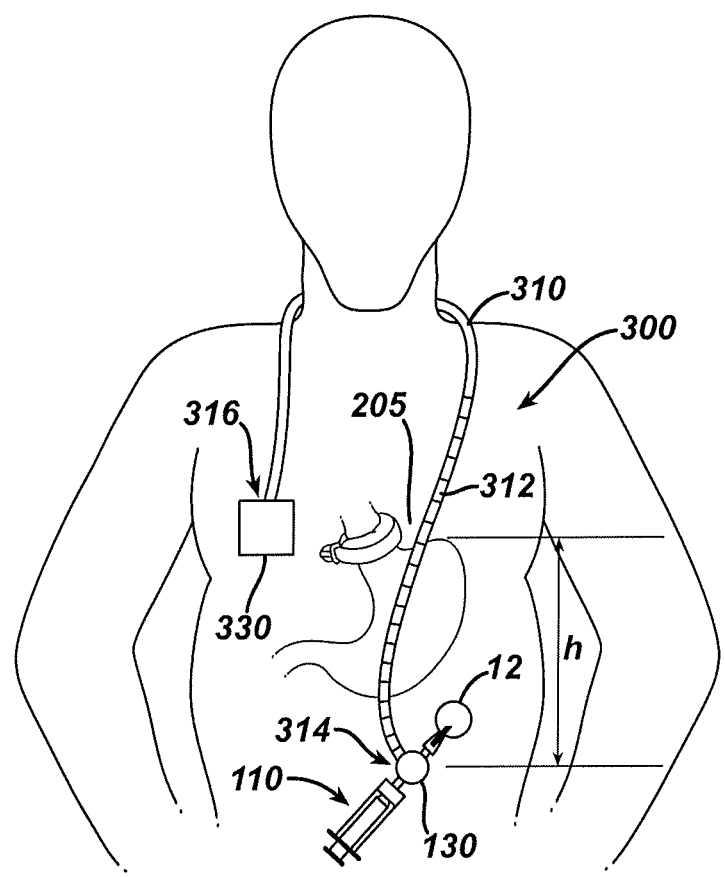
FIG. 8 depicts a front view of a patient and an alternate exemplary measurement device.

FIG. 8 depicts an exemplary alternative version of a measurement device (300). Measurement device (300) is substantially similar to measurement device (200) shown in FIGS. 6 and 7 and described above, therefore the majority of the description will not be repeated. Measurement device (300) comprises a cable (310) that incorporates a plurality of equally spaced markings (312) that may be used to indicate distance, similar to cable (210) and markings (212) described above. Cable (310) may be selectively engaged with pressure sensing component (130) at a first end (314). Cable (210) may include a boot portion (not shown) similar to boot portion (164) configured to couple cable (210) and pressure sensing component (130). Cable (310) may further be selectively engaged with a wireless transmitter (330) at a second end (316). Wireless transmitter (330) may be configured to wirelessly communicate with a display device, including but not limited to display device (150). Accordingly, cable (310) may be operable to communicate data obtained by pressure sensor (138) to a display device, although this is not required. Cable (310) may comprise a conventional USB cable or some other type of cable. Wireless transmitter (330) may be configured to provide wireless communication using any suitable conventional components and techniques (e.g., wi-fi communication, other types of RF communication, infrared communication, etc.).

Wireless transmitter (330) may further function as a counter-weight to enhance the support provided by cable (310) with regard to the weight of syringe (110). In some versions, the weight of wireless communication components within wireless transmitter (330) may suffice to provide a suitable counterweight against syringe (110). In some other versions, additional weight may be added to wireless transmitter (330) to provide a suitable counterweight against syringe (110). Cable (310) may be configured and oriented around a patient's neck, similar to cable (210), such that the portion of cable (310) containing markings (312) is aligned to measure the height difference between pressure sensing portion (130) and the patient's xyphoid (205). Also, similar to cable (210), other suitable configurations and orientations where markings (312) on cable (310) are aligned with the distance between pressure sensing component (130) and xyphoid (205) and/or where cable (310) supports at least a portion of the weight of syringe (110) will be apparent to those skilled in the art in view of the teachings herein. Similarly, other suitable variations of cable (210), including but not limited to alternative functionalities, features, components, structures, configurations, substitutes, and supplements for cable (310), will be apparent to those of ordinary skill in the art in view of the teachings herein.

Pressure data obtained using pressure sensing component (130) may be processed and presented on display device (150) in a variety of ways. In addition, the user may react to such pressure data in a variety of ways. Various suitable ways in which pressure data may be processed, presented, and reacted to are disclosed in U.S. Pub. No. 2008/0250340, entitled "GUI for an Implantable Restriction Device and Data Logger," published Oct. 9, 2008, the disclosure of which is incorporated by reference herein. Other ways in which pressure data may be processed, presented, and reacted to are disclosed in U.S. Pub. No. 2006/0211914, and issued Aug. 17, 2010 as U.S. Pat. No. 7,775,215, entitled "System and Method for Determining Implanted Device Positioning and Obtaining Pressure Data," published Sep. 21, 2006, the disclosure of which is incorporated by reference herein. Still other suitable ways in which pressure data may be processed, presented, and reacted to will be apparent to those of ordinary skill in the art in view of the teachings herein.

Figure 9:
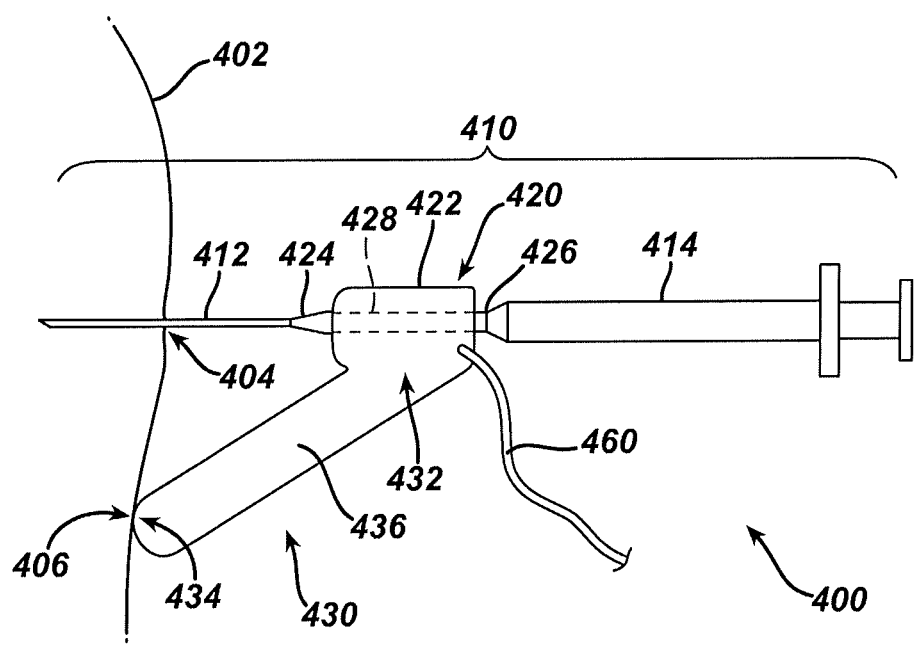
FIG. 9 depicts a side view of a needle system and an exemplary support apparatus.

FIG. 9 illustrates another exemplary fluid adjustment system (400). As shown, fluid adjustment system (400) comprises a needle system (410) and a stabilizer or support apparatus (430). In this example, needle system (410) comprises a needle (412), a needle accessory (414), and a housing (420). It will be appreciated that needle system (410) may comprise (and housing (420) may be configured to engage) more than one needle accessory (414). Needle (412) may be configured to pierce an injection surface (402), such as a patient's skin, at an injection point (404) and be inserted into an implanted device, such as port (12). Needle (412) may comprise a Huber needle or any other suitable type of needle. Needle accessory (414) may comprise a syringe barrel, as shown in FIG. 9, or any other suitable device configured to be used in conjunction with needle (412), including but not limited to a piece of tubing and/or a stopcock valve (e.g., stopcock valve leads to a pressure sensor and/or syringe barrel via tubing, etc.). Needle system (410) may be similar to needle system (100) described above. Specifically, needle (412) may be substantially analogous to needle (120), needle accessory (414) may be substantially analogous to syringe (110), and housing (420) may be substantially analogous to body portion (132) described above, although this is not required.

In the illustrated example, housing (420) comprises a body portion (422), a needle connector (424), an accessory connector (426), and an internal conduit (428). Body portion (422) may be similar to the above-described body portion (132), needle connector (424) may be similar to the above-described lower luer lock portion (136), and accessory connector (426) may be similar to the above-described upper luer lock portion (134), although this is not required. As shown, needle connector (424) is configured to engage needle (412). Needle connector (424) may comprise any suitable structure configured to selectively, releasably, or fixedly engage needle (412). In this example, accessory connector (426) is configured to engage needle accessory (414). Accessory connector (426) may comprise any suitable structure configured to selectively, releasably, or fixedly engage needle accessory (414). In some versions (not shown), housing (420) may comprise more than one accessory connector to engage multiple needle accessories. As shown in FIG. 9, conduit (428) is configured to provide fluid communication between needle connector (424) and accessory connector (426). Accordingly, when needle system (410) is assembled, conduit (428) provides fluid communication between needle (412) and needle accessory (414).

Housing (420) may further comprise a pressure sensor, such as pressure sensor (138), that is in fluid communication with conduit (428), such that the pressure sensor is operable to sense the pressure of fluid in needle accessory (414) and needle (412). Of course, in some versions a pressure sensor may be omitted. In the present example, housing (420) is engaged with a cable (460) that may be substantially analogous to cable (160) described above. Cable (460) may be in communication with a pressure sensor in housing (420) and thereby communicate pressure readings obtained by the pressure sensor along cable (460). Cable (460) may be in communication with a display device, such as display device (150), via a physical or wireless connection with the display device. Cable (460) may be omitted in some versions, such as versions where the pressure sensor is omitted or versions where a pressure sensor in housing (420) is operable to wirelessly communicate with a display device.

As shown in FIG. 9, support apparatus (430) comprises a proximal portion (432), a distal portion (434), and a connecting member (436). Support apparatus (430) may be configured to at least partially support needle system (410) by abutting and engaging a support surface, such as injection surface (402) (e.g., the patient's skin) In some versions, support apparatus (430) may be configured to provide adequate support to needle system (410) in order to allow needle system (410) to remain substantially perpendicular to injection surface (402) without additional external support for needle system (410), including but not limited to a user holding on to needle system (410). Furthermore, support apparatus (430) may be configured to provide adequate support to allow a patient to sit upright and/or stand with needle (412) inserted into an implanted device (e.g., injection port (12)) without the need for additional external support for needle system (410).

In this example, proximal portion (432) is unitarily engaged with body portion (422). Proximal portion (432) may be selectively, releasably, or fixedly engaged with body portion (422). In some versions, support apparatus (430) is integral with body portion (422) to form a single-piece rigid component. In the present example, support apparatus (430) is angled relative to the longitudinal axis of needle (412) such that distal portion (434) of support apparatus (430) engages injection surface (402) at an engagement point (406) upon insertion of needle (412) through injection surface (402). In this example engagement point (406) is located below injection point (404). The angle between support apparatus (430) and the longitudinal axis of needle (412) may be fixed or adjustable. Distal portion (434) may incorporate one or more gripping features configured to facilitate engagement between support apparatus (430) and injection surface (402), including but not limited to ribs, knurling, elastomeric material, adhesive, one or more suction cups, and/or clips, etc. In addition, the length of connecting member (436) may be fixed. Alternatively, connecting member (436) may comprise a telescoping member or otherwise comprise an adjustable length member such that the length of support apparatus (430) may be adjusted to accommodate needles of different lengths and/or different insertion depths. Furthermore, while housing (420) has just one support apparatus (430) in the present example, it should be understood that housing (420) may alternatively have more than one support apparatus (430) if desired. Still other suitable variations of fluid adjustment system (400), including but not limited to alternative functionalities, features, components, structures, configurations, substitutes, and supplements for fluid adjustment system (400), will be apparent to those of ordinary skill in the art in view of the teachings herein.

Figure 10:
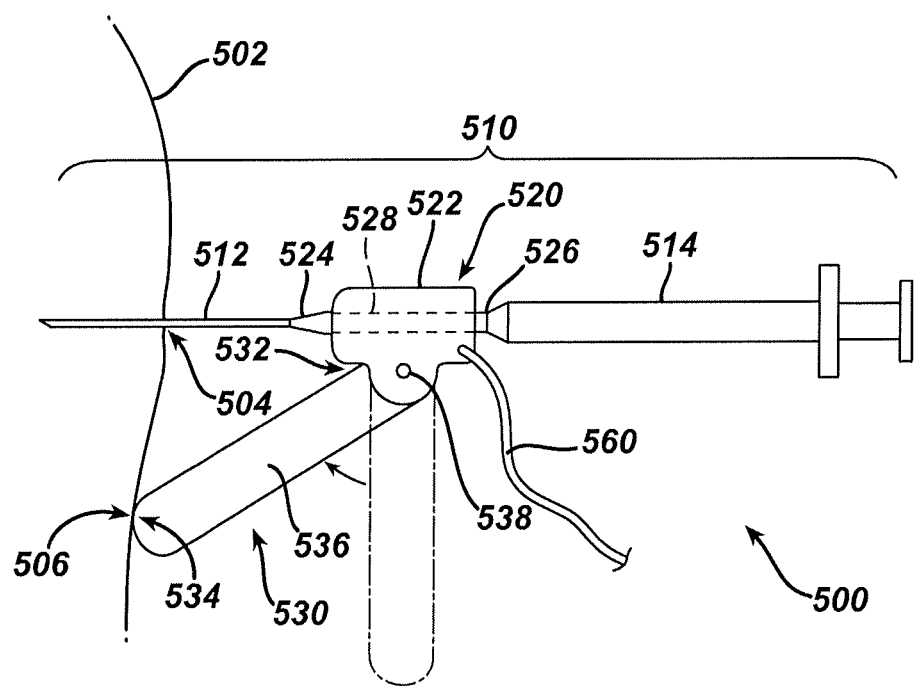
FIG. 10 depicts a side view of a needle system and an exemplary alternative support apparatus.

FIG. 10 illustrates another exemplary fluid adjustment system (500). As shown, fluid adjustment system (500) comprises a needle system (510) and a stabilizer or support apparatus (530). Fluid adjustment system (500) may be substantially similar to fluid adjustment system (400) described above. In this example, needle system (510) comprises a needle (512), a needle accessory (514), and a housing (520). It will be appreciated that needle system (510) may comprise (and housing (520) may be configured to engage) more than one needle accessory (514). Needle (512) may be configured to pierce an injection surface (502), such as a patient's skin, at an injection point (504) and be inserted into an implanted device, such as port (12). Needle (512) may comprise a Huber needle or any other suitable type of needle. Needle accessory (514) may comprise a syringe barrel, as shown in FIG. 10, or any other suitable device configured to be used in conjunction with needle (512), including but not limited to a piece of tubing and/or a stopcock valve (e.g., stopcock valve leads to a pressure sensor and/or syringe barrel via tubing, etc.). Needle system (510) may be similar to needle system (100) described above. Specifically, needle (512) may be substantially analogous to needle (120), needle accessory (514) may be substantially analogous to syringe (110), and housing (520) may be substantially analogous to body portion (132) described above, although this is not required.

In the illustrated example, housing (520) comprises a body portion (522), a needle connector (524), an accessory connector (526), and an internal conduit (528). Body portion (522) may be similar to the above-described body portion (132), needle connector (524) may be similar to the above-described lower luer lock portion (136), and accessory connector (526) may be similar to the above-described upper luer lock portion (134), although this is not required. As shown, needle connector (524) is configured to engage needle (512). Needle connector (524) may comprise any suitable structure configured to selectively, releasably, or fixedly engage needle (512). In this example, accessory connector (526) is configured to engage needle accessory (514). Accessory connector (526) may comprise any suitable structure configured to selectively, releasably, or fixedly engage needle accessory (514). In some versions (not shown), housing (520) may comprise more than one accessory connector to engage multiple needle accessories. As shown in FIG. 10, conduit (528) is configured to provide fluid communication between needle connector (524) and accessory connector (526). Accordingly, when needle system (510) is assembled, conduit (528) provides fluid communication between needle (512) and needle accessory (514).

Housing (520) may further comprise a pressure sensor, such as pressure sensor (138), that is in fluid communication with conduit (528), such that the pressure sensor is operable to sense the pressure of fluid in needle accessory (514) and needle (512). Of course, in some versions a pressure sensor may be omitted. In the present example, housing (520) is engaged with a cable (560) that may be substantially analogous to cable (160) described above. Cable (560) may be in communication with a pressure sensor in housing (520) and thereby communicate pressure readings obtained by the pressure sensor along cable (560). Cable (560) may be in communication with a display device, such as display device (150), via a physical or wireless connection with the display device. Cable (560) may be omitted in some versions, such as versions where the pressure sensor is omitted or where a pressure sensor in housing (520) is operable to wirelessly communicate with a display device.

As shown in FIG. 10, support apparatus (530) comprises a proximal portion (532), a distal portion (534), and a connecting member (536). Support apparatus (530) may be configured to at least partially support needle system (510) by abutting and engaging a support surface, such as injection surface (502) (e.g., the patient's skin). In some versions, support apparatus (530) may be configured to provide adequate support to needle system (510) in order to allow needle system (510) to remain substantially perpendicular to injection surface (502) without additional external support for needle system (510), including but not limited to a user holding on to needle system (510). Furthermore, support apparatus (530) may be configured to provide adequate support to allow a patient to sit upright and/or stand with needle (512) inserted into an implanted device (e.g., injection port (12)) without the need for additional external support for needle system (510).

In this example, proximal portion (532) is rotatably engaged with body portion (522). Proximal portion (532) may be selectively, releasably, or fixedly engaged with body portion (522). Support apparatus (530) may be engaged with body portion (522) via any suitable mechanism configured to allow support apparatus to rotate, including but not limited to a hinge, a living hinge, a pin, a spring-loaded hinge mechanism, and a ratcheting mechanism. As shown, support apparatus (530) is angled relative to the longitudinal axis of needle (512) such that distal portion (534) of support apparatus (530) engages injection surface (502) at an engagement point (506) upon insertion of needle (512) through injection surface (502). In the present example, support apparatus (530) is rotatable about pin (538), such that the user may selectively adjust the angle defined between support apparatus (530) and housing (520) to provide adequate support. In this example, engagement point (506) is located below injection point (504). Distal portion (534) may incorporate one or more gripping features configured to facilitate engagement between support apparatus (530) and injection surface (502), including but not limited to ribs, knurling, elastomeric material, adhesive, one or more suction cups, and/or clips, etc. In addition, the length of connecting member (536) may be fixed. Alternatively, connecting member (536) may comprise a telescoping member or otherwise comprise an adjustable length member such that the length of support apparatus (530) may be adjusted to accommodate needles of different lengths and/or different insertion depths. Furthermore, while housing (520) has just one support apparatus (530) in the present example, it should be understood that housing (520) may alternatively have more than one support apparatus (530) if desired. Still other suitable variations of fluid adjustment system (500), including but not limited to alternative functionalities, features, components, structures, configurations, substitutes, and supplements for fluid adjustment system (500), will be apparent to those of ordinary skill in the art in view of the teachings herein.

Figure 11:
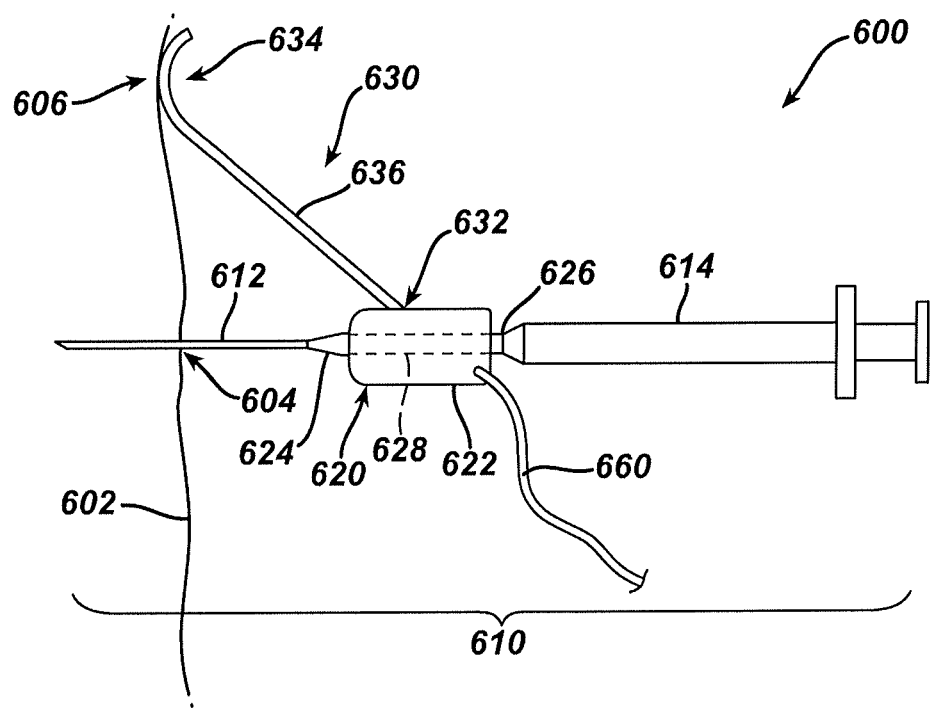
FIG. 11 depicts a side view of a needle system and another exemplary alternative support apparatus.

FIG. 11 illustrates another exemplary fluid adjustment system (600). As shown, fluid adjustment system (600) comprises a needle system (610) and a stabilizer or support apparatus (630). Fluid adjustment system (600) may be substantially similar to fluid adjustment systems (400, 500) described above. In this example, needle system (610) comprises a needle (612), a needle accessory (614), and a housing (620). It will be appreciated that needle system (610) may comprise (and housing (620) may be configured to engage) more than one needle accessory (514). Needle (612) may be configured to pierce an injection surface (602), such as a patient's skin, at an injection point (604) and be inserted into an implanted device, such as port (12). Needle (612) may comprise a Huber needle or any other suitable type of needle. Needle accessory (614) may comprise a syringe barrel, as shown in FIG. 11, or any other suitable device configured to be used in conjunction with needle (612), including but not limited to a piece of tubing and/or a stopcock valve (e.g., stopcock valve leads to a pressure sensor and/or syringe barrel via tubing, etc.). Needle system (610) may be similar to needle system (100) described above. Specifically, needle (612) may be substantially analogous to needle (120), needle accessory (614) may be substantially analogous to syringe (110), and housing (620) may be substantially analogous to body portion (132) described above, although this is not required.

In the illustrated example, housing (620) comprises a body portion (622), a needle connector (624), an accessory connector (626), and an internal conduit (628). Body portion (622) may be similar to the above-described body portion (132), needle connector (624) may be similar to the above-described lower luer lock portion (136), and accessory connector (626) may be similar to the above-described upper luer lock portion (134), although this is not required. As shown, needle connector (624) is configured to engage needle (612). Needle connector (624) may comprise any suitable structure configured to selectively, releasably, or fixedly engage needle (612). In this example, accessory connector (626) is configured to engage needle accessory (614). Accessory connector (626) may comprise any suitable structure configured to selectively, releasably, or fixedly engage needle accessory (614). In some versions (not shown), housing (620) may comprise more than one accessory connector to engage multiple needle accessories. As shown in FIG. 11, conduit (628) is configured to provide fluid communication between needle connector (624) and accessory connector (626). Accordingly, when needle system (610) is assembled, conduit (628) provides fluid communication between needle (612) and needle accessory (614).

Housing (620) may further comprise a pressure sensor, such as pressure sensor (138), that is in fluid communication with conduit (628), such that the pressure sensor is operable to sense the pressure of fluid in needle accessory (614) and needle (612). Of course, in some versions a pressure sensor may be omitted. In the present example, housing (620) is engaged with a cable (660) that may be substantially analogous to cable (160) described above. Cable (660) may be in communication with a pressure sensor in housing (620) and thereby communicate pressure readings obtained by the pressure sensor along cable (660). Cable (660) may be in communication with a display device, such as display device (150), via a physical or wireless connection with the display device. Cable (660) may be omitted in some versions, such as versions where the pressure sensor is omitted or where a pressure sensor in housing (620) is operable to wirelessly communicate with a display device.

As shown in FIG. 11, support apparatus (630) comprises a proximal portion (632), a distal portion (634), and a connecting member (636). Support apparatus (630) may be configured to at least partially support needle system (610) by abutting and engaging a support surface, such as injection surface (602) (e.g., the patient's skin). In some versions, support apparatus (630) may be configured to provide adequate support to needle system (610) in order to allow needle system (610) to remain substantially perpendicular to injection surface (602) without additional external support for needle system (610), including but not limited to a user holding on to needle system (610). Furthermore, support apparatus (630) may be configured to provide adequate support to allow a patient to sit upright and/or stand with needle (612) inserted into an implanted device (e.g., injection port (12)) without additional external support for needle system (610).

In this example, proximal portion (632) is engaged with body portion (622). Proximal portion (632) may be selectively, releasably, or fixedly engaged with body portion (622). In the illustrated version, support apparatus (630) comprises a tensile member configured to be stretched by a user such that distal portion (634) may engage injection surface (604). The tensile nature of support apparatus (630) may allow the user to adjust the length of support apparatus (630) to accommodate needles of different lengths and/or different insertion depths. In addition to or as an alternative to having such tensile properties, support apparatus (630) may be malleable to allow the user to adjust the effective length of support apparatus (630) to accommodate needles of different lengths and/or different insertion depths. As shown, support apparatus (630) is angled relative to the longitudinal axis of needle (612) such that distal portion (634) of support apparatus (630) engages injection surface (602) at an engagement point (606) upon insertion of needle (612) through injection surface (602). In this example, engagement point (606) is located above injection point (604). Distal portion (634) may comprise any suitable structure or device configured to enhance or facilitate engagement of distal portion (634) with injection surface (602), including but not limited to ribs, knurling, elastomeric material, adhesive, one or more suction cups, and/or clips, etc. While housing (620) has just one support apparatus (630) in the present example, it should be understood that housing (620) may alternatively have more than one support apparatus (630) if desired. Still other suitable variations of fluid adjustment system (600), including but not limited to alternative functionalities, features, components, structures, configurations, substitutes, and supplements for fluid adjustment system (600), will be apparent to those of ordinary skill in the art in view of the teachings herein.

Figure 12:
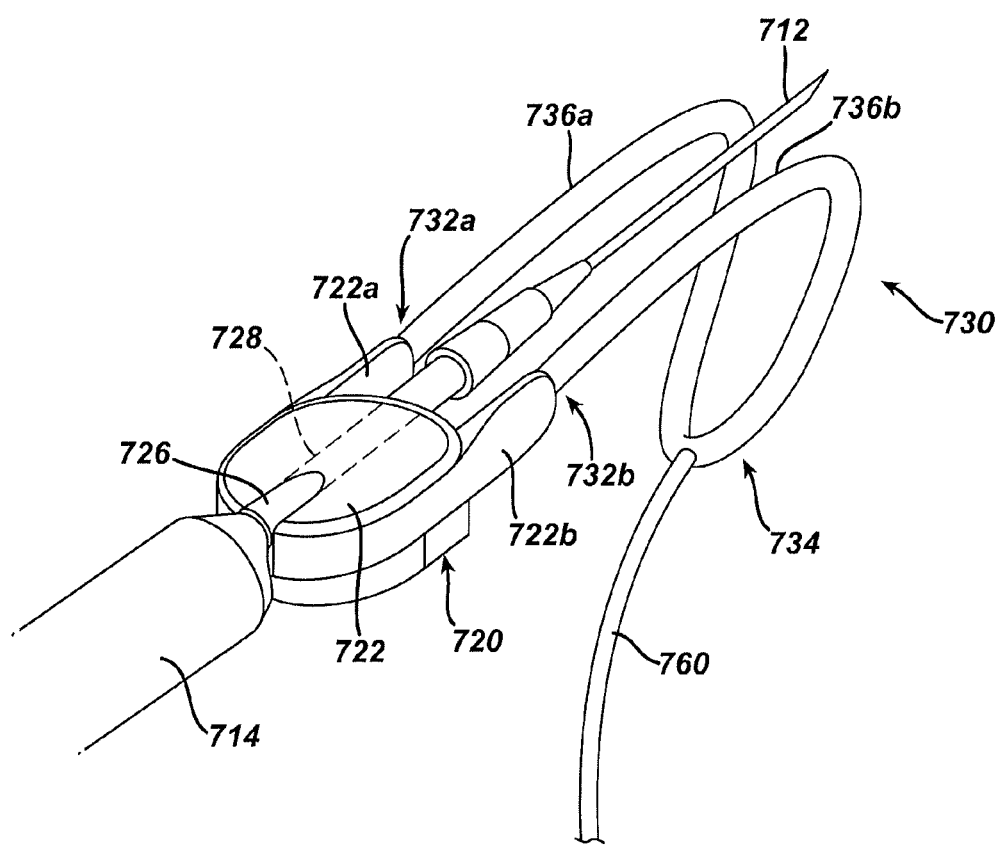
FIG. 12 depicts a perspective view of a needle system and another exemplary alternative support apparatus.
Figure 13:
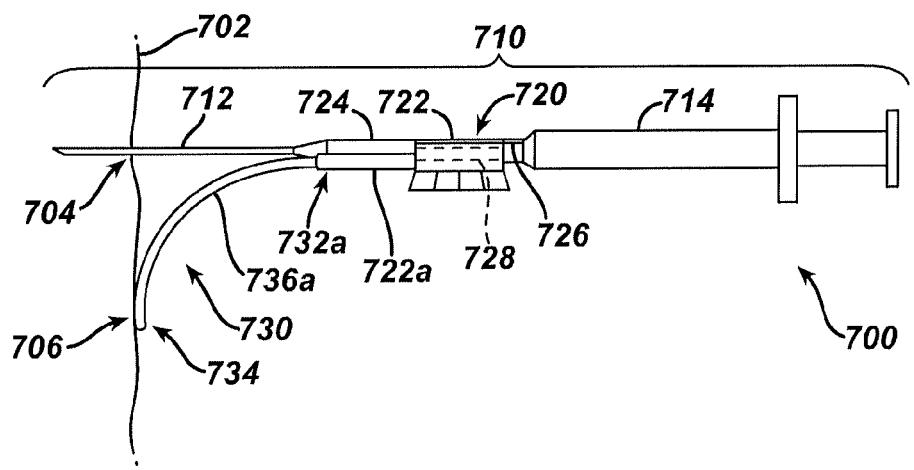
FIG. 13 depicts a side view of the support apparatus of FIG. 12.

FIGS. 12-13 illustrate another exemplary fluid adjustment system (700). As shown, fluid adjustment system (700) comprises a needle system (710) and a stabilizer or support apparatus (730). Fluid adjustment system (700) may be substantially similar to fluid adjustment systems (400, 500, 600) described above. In this example, needle system (710) comprises a needle (712), a needle accessory (714), and a housing (720). It will be appreciated that needle system (710) may comprise (and housing (720) may be configured to engage) more than one needle accessory. Needle (712) may be configured to pierce an injection surface (702), such as a patient's skin, at an injection point (704) and be inserted into an implanted device, such as port (12). Needle (712) may comprise a Huber needle or any other suitable type of needle. Needle accessory (714) may comprise a syringe barrel, as shown in FIGS. 12-13, or any other suitable device configured to be used in conjunction with needle (712), including but not limited to a piece of tubing and/or a stopcock valve (e.g., stopcock valve leads to a pressure sensor and/or syringe barrel via tubing, etc.). Needle system (710) may be similar to needle system (100) described above. Specifically, needle (712) may be substantially analogous to needle (120), needle accessory (714) may be substantially analogous to syringe (110), and housing (720) may be substantially analogous to body portion (132) described above, although this is not required.

In the illustrated example, housing (720) comprises a body portion (722), a needle connector (724), an accessory connector (726), and an internal conduit (728). Body portion (722) may be similar to the above-described body portion (132), needle connector (724) may be similar to the above-described lower luer lock portion (136), and accessory connector (726) may be similar to the above-described upper luer lock portion (134), although this is not required. As shown, needle connector (724) is configured to engage needle (712). Needle connector (724) may comprise any suitable structure configured to selectively, releasably, or fixedly engage needle (712). In this example, accessory connector (726) is configured to engage needle accessory (714). Accessory connector (726) may comprise any suitable structure configured to selectively, releasably, or fixedly engage needle accessory (714). In some versions (not shown), housing (720) may comprise more than one accessory connector to engage multiple needle accessories. As shown in FIGS. 12-13, conduit (728) is configured to provide fluid communication between needle connector (724) and accessory connector (726). Accordingly, when needle system (710) is assembled, conduit (728) provides fluid communication between needle (712) and needle accessory (714).

Housing (720) may further comprise a pressure sensor, such as pressure sensor (138), that is in fluid communication with conduit (728), such that the pressure sensor is operable to sense the pressure of fluid in needle accessory (714) and needle (712). Of course, in some versions a pressure sensor may be omitted. In the present example, support apparatus (730) is engaged with a cable (760) that may be substantially analogous to cable (160) described above. Alternatively, cable (760) may be engaged directly with housing (720) similar to the examples described above. Cable (760) may be in communication with a pressure sensor in housing (720) and thereby communicate pressure readings obtained by the pressure sensor along cable (760). Cable (760) may be in communication with a display device, such as display device (150), via a physical or wireless connection with the display device. Cable (760) may be omitted in some versions, such as versions where the pressure sensor is omitted or where a pressure sensor in housing (720) is operable to wirelessly communicate with a display device.

As shown in FIGS. 12-13, body portion (722) further comprises a first arm (722a) and a second arm (722b) that extend distally from the sides of body portion (722) and engage support apparatus (730). Support apparatus (730) of this example comprises a closed loop member incorporating a first proximal portion (732a); a second proximal portion (732b); a distal portion (734) or loop portion; a first connecting member (736a) extending between first proximal portion (732a) and distal portion (734); and a second connecting member (736b) extending between second proximal portion (732b) and distal portion (734). Support apparatus (730) may be configured to at least partially support needle system (710) by abutting and engaging a support surface, such as injection surface (702) (e.g., the patient's skin). In some versions, support apparatus (730) may be configured to provide adequate support to needle system (710) in order to allow needle system (710) to remain substantially perpendicular to injection surface (702) without additional external support for needle system (710), including but not limited to a user holding on to needle system (710). Furthermore, support apparatus (730) may be configured to provide adequate support to allow a patient to sit upright and/or stand with needle (712) inserted into an implanted device (e.g., injection port (12)) without additional external support for needle system (710).

In the present example, first proximal portion (732a) of support apparatus (730) is engaged with first arm (722a) of housing (720), and second proximal portion (732b) is engaged with second arm (722b) of housing (720). First proximal portion (732a) may be selectively, releasably, or fixedly engaged with first arm (722a). Similarly, second proximal portion (732b) may be selectively, releasably, or fixedly engaged with second arm (722b). As shown in FIGS. 12-13, support apparatus (730) is formed of a malleable material that is configured to be manipulated and shaped by a user such that a portion of support apparatus (730), such as distal portion (734), engages injection surface (604). The malleable nature of support apparatus (630) may allow the user to adjust the length and shape of support apparatus (630) to accommodate needles of different lengths and/or different insertion depths. As shown, support apparatus (730) is angled relative to the longitudinal axis of needle (712) such that distal portion (734) of support apparatus (730) engages injection surface (702) at an engagement point (706) upon insertion of needle (712) through injection surface (702). In this example, engagement point (706) is located below injection point (704).

Those skilled in the art will recognize that support apparatus (730) may be adjusted such that any suitable portion of support apparatus (730) engages injection surface. By way of example only, support apparatus (730) may be adjusted such that a portion of first connecting member (736a) and/or second connecting member (736b) engages injection surface rather than distal portion (734). It should also be understood that support apparatus (730) may be adjusted such that needle (712) penetrates the patient's skin at any suitable angle (e.g., where injection port (12) is oriented such that it is not substantially parallel to the patient's skin, etc.). Distal portion (734) may incorporate one or more gripping features configured to facilitate engagement between support apparatus (730) and injection surface (702), including but not limited to ribs, knurling, elastomeric material, adhesive, one or more suction cups, and/or clips, etc. Still other suitable variations of fluid adjustment system (700), including but not limited to alternative functionalities, features, components, structures, configurations, substitutes, and supplements for fluid adjustment system (700), will be apparent to those of ordinary skill in the art in view of the teachings herein.

Figure 14:
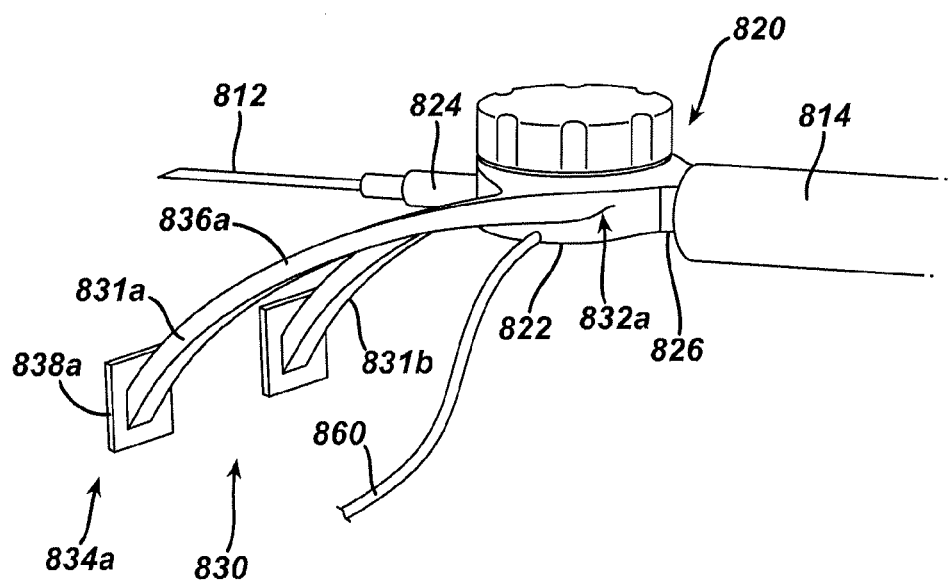
FIG. 14 depicts a perspective view of a needle system and another exemplary alternative support apparatus.
Figure 15:
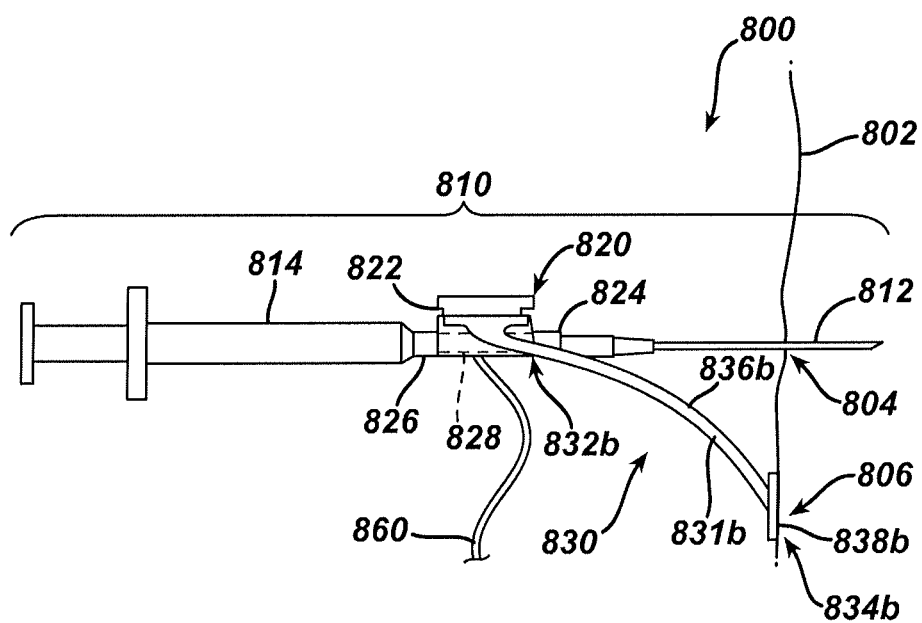
FIG. 15 depicts a side view of the support apparatus of FIG. 14.

FIGS. 14-15 illustrate another exemplary fluid adjustment system (800). As shown, fluid adjustment system (800) comprises a needle system (810) and a stabilizer or support apparatus (830). Fluid adjustment system (800) may be substantially similar to fluid adjustment systems (400, 500, 600, 700) described above. In this example, needle system (810) comprises a needle (812), a needle accessory (814), and a housing (820). It will be appreciated that needle system (810) may comprise (and housing (820) may be configured to engage) more than one needle accessory. Needle (812) may be configured to pierce an injection surface (802), such as a patient's skin, at an injection point (804) and be inserted into an implanted device, such as port (12). Needle (812) may comprise a Huber needle or any other suitable type of needle. Needle accessory (814) may comprise a syringe barrel, as shown in FIGS. 14-15, or any other suitable device configured to be used in conjunction with needle (812), including but not limited to a piece of tubing and/or a stopcock valve (e.g., stopcock valve leads to a pressure sensor and/or syringe barrel via tubing, etc.). Needle system (810) may be similar to needle system (100) described above. Specifically, needle (812) may be substantially analogous to needle (120), needle accessory (814) may be substantially analogous to syringe (110), and housing (820) may be substantially analogous to body portion (132) described above, although this is not required.

In the illustrated example, housing (820) comprises a body portion (822), a needle connector (824), an accessory connector (826), and an internal conduit (828). Body portion (822) may be similar to the above-described body portion (132), needle connector (824) may be similar to the above-described lower luer lock portion (136), and accessory connector (826) may be similar to the above-described upper luer lock portion (134), although this is not required. As shown, needle connector (824) is configured to engage needle (812). Needle connector (824) may comprise any suitable structure configured to selectively, releasably, or fixedly engage needle (812). In this example, accessory connector (826) is configured to engage needle accessory (814). Accessory connector (826) may comprise any suitable structure configured to selectively, releasably, or fixedly engage needle accessory (814). In some versions (not shown), housing (820) may comprise more than one accessory connector to engage multiple needle accessories. As shown in FIGS. 14-15, conduit (828) is configured to provide fluid communication between needle connector (824) and accessory connector (826). Accordingly, when needle system (810) is assembled, conduit (828) provides fluid communication between needle (812) and needle accessory (814).

Housing (820) may further comprise a pressure sensor, such as pressure sensor (138), that is in fluid communication with conduit (828), such that the pressure sensor is operable to sense the pressure of fluid in needle accessory (814) and needle (812). Of course, in some versions the pressure sensor may be omitted. In the present example, housing (820) is engaged with a cable (860) that may be substantially to cable (160) described above. Cable (860) may be in communication with a pressure sensor in housing (820) and thereby communicate pressure readings obtained by the pressure sensor along cable (860). Cable (860) may be in communication with a display device, such as display device (150), via a physical or wireless connection with the display device. Cable (860) may be omitted in some versions, such as versions where the pressure sensor is omitted or where a pressure sensor in housing (820) is operable to wirelessly communicate with a display device.

As shown in FIGS. 14-15, support apparatus (830) comprises a first support member (831a) and a second support member (831b). In this example, first support member (831a) comprises a proximal portion (832a), a distal portion (834a), and a connecting member (836a). Similarly, second support member (831b) comprises a proximal portion (832b), a distal portion (834b), and a connecting member (836b). Support apparatus (830) may be configured to at least partially support needle system (810) by abutting and engaging a support surface, such as injection surface (802) (e.g., the patient's skin). In some versions, support apparatus (830) may be configured to provide adequate support to needle system (810) in order to allow needle system (810) to remain substantially perpendicular to injection surface (802) without additional external support for needle system (810), including but not limited to a user holding on to needle system (810). Furthermore, support apparatus (830) may be configured to provide adequate support to allow a patient to sit upright and/or stand with needle (812) inserted into an implanted device (e.g., injection port (12)) without additional external support for needle system (810).

In the present example, proximal portion (832a) of first support member (831a) is engaged with a first side of body portion (822), and proximal portion (832b) of second support member (831b) is engaged with an opposite side of body portion (822). Of course, first support member (831a) and second support member (831b) may be engaged with body portion (822) at any suitable location. First proximal portion (832a) of first support member (831a) may be selectively, releasably, or fixedly engaged with body portion (822). Similarly, proximal portion (832b) of second support member (831b) may be selectively, releasably, or fixedly engaged with body portion (822). First support member (831a) and second support member (831b) may comprise any suitable material, including but not limited to a malleable material. As shown in FIGS. 14-15, distal portion (834a) of first support member (831a) comprises an engagement pad (838a), and distal portion (834b) of second support member (831b) comprises an engagement pad (838b). Engagement pads (838a, 838b) may be configured to abut and engage injection surface (802) in order to support needle system (810). As shown, support apparatus (830) is angled relative to the longitudinal axis of needle (812) such that distal portions (834a, 834b) of support apparatus (830) engage injection surface (802) at engagement points (806) upon insertion of needle (812) through injection surface (802). In the present example, engagement points (806) are located below injection point (804). Distal portions (834a, 834b), and more specifically engagement pads (838a, 838b), may incorporate one or more gripping features configured to facilitate engagement between support apparatus (830) and injection surface (802), including but not limited to ribs, knurling, elastomeric material, adhesive, one or more suction cups, and/or clips, etc.

In addition, the length of first support member (831a) and second support member (831b), and, consequently support apparatus (830) may be fixed. Alternatively, first support member (831a) and second support member (831b) may each comprise a telescoping member or otherwise comprise an adjustable length member such that the length of support apparatus (830) may be adjusted to accommodate needles of different lengths and/or different insertion depths. In addition or in the alternative, the malleable nature of support apparatus (830) of the present example may allow the user to adjust the length and shape of support apparatus (830) to accommodate needles of different lengths and/or different insertion depths. It should also be understood that support apparatus (830) may be adjusted such that needle (812) penetrates the patient's skin at any suitable angle (e.g., where injection port (12) is oriented such that it is not substantially parallel to the patient's skin, etc.). Still other suitable variations of fluid adjustment system (800), including but not limited to alternative functionalities, features, components, structures, configurations, substitutes, and supplements for fluid adjustment system (800), will be apparent to those of ordinary skill in the art in view of the teachings herein.

Figure 16:
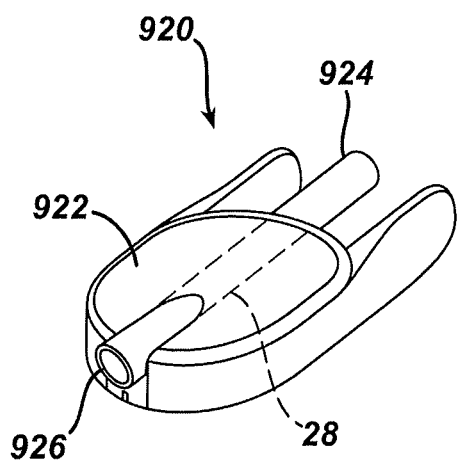
FIG. 16 depicts a perspective view of an exemplary housing.

FIG. 16 illustrates an exemplary housing (920). Housings (420, 520, 620, 720, 820) described above may comprise housing (920), although this is not required. As shown, housing (920) comprises a body portion (922), a needle connector (924), an accessory connector (926), and a conduit (928). Body portion (922) may be substantially analogous to body portion (132), needle connector (924) may be substantially analogous to lower luer lock portion (136), and accessory connector (926) may be substantially analogous to upper luer lock portion (134) described above, although this is not required. As shown, needle connector (924) is configured to engage a needle. Needle connector (924) may comprise any suitable structure (e.g., luer lock feature, etc.) configured to selectively, releasably, or fixedly engage a needle. In this example, accessory connector (926) is configured to engage a needle accessory. Accessory connector (926) may comprise any suitable structure (e.g., luer lock feature, etc.) configured to selectively, releasably, or fixedly engage a needle accessory. In some versions (not shown), housing (920) may comprise more than one accessory connector to engage multiple needle accessories. As shown in FIG. 16, an internal conduit (928) is configured to provide fluid communication between needle connector (924) and accessory connector (926). Accordingly, when a needle system is assembled, conduit (928) provides fluid communication between a needle and needle accessory engaged with housing (920). Housing (920) may also contain a pressure sensor, such as pressure sensor (138), that is in fluid communication with conduit (928), such that the pressure sensor is operable to sense the pressure of fluid in a needle accessory and a needle engaged with housing (920). Of course, in some versions the pressure sensor may be omitted. Still other suitable variations of housing (920), including but not limited to alternative functionalities, features, components, structures, configurations, substitutes, and supplements for housing (920), will be apparent to those of ordinary skill in the art in view of the teachings herein.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

It will also be readily apparent to those skilled in the art that examples described herein may have applicability to other types of devices (i.e., not just implantable bands per se). For instance, a syringe (110) and needle (120) fitted with a pressure sensing component (130) may be used to adjust the pressure of fluid within a gastric balloon or other volume occupying device; the pressure of fluid within an infusion port; etc. In addition, a support apparatus, such as support apparatuses (430, 530, 630, 730, 830) may be used in conjunction with a syringe to adjust the fluid within a gastric balloon or other volume occupying device, etc. Various other types of devices and systems with which the examples described herein may be used will be apparent to those of ordinary skill in the art.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A housing comprising:
   (a) a body portion, wherein the body portion comprises:
      (i) a needle connector, wherein the needle connector is configured to couple with a needle, wherein the needle defines a longitudinal axis,
      (ii) an accessory connector, wherein the accessory connector is configured to couple with a syringe, and
      (iii) a conduit, wherein the conduit is configured to provide fluid communication between the needle connector and the accessory connector; and
   (b) a support apparatus, wherein the support apparatus comprises:
      (i) a proximal portion, wherein the proximal portion is engaged with the body portion,
      (ii) a distal portion, wherein the distal portion is configured to abut a support surface distal to the needle connector, and
      (iii) a connecting member, wherein the connecting member extends between the proximal portion and the distal portion such that the proximal portion and the distal portion are fixed relative to the longitudinal axis,
   wherein the support apparatus is rotatably engaged with the body portion.

2. The housing of claim 1, further comprising a pressure sensor, wherein the pressure sensor is in fluid communication with the conduit, wherein the pressure sensor is operable to sense the pressure of fluid in the needle.

3. The housing of claim 2, further comprising a cable in communication with the pressure sensor, wherein the cable is configured to transmit pressure data from the pressure sensor to an external display device.

4. The housing of claim 1, wherein the support apparatus is formed unitarily with the body portion.

5. The housing of claim 1, wherein the support apparatus comprises a tensile member configured to stretch to alter the length of the connecting member.

6. The housing of claim 1, wherein the support apparatus comprises a malleable member.

7. The housing of claim 6, wherein the support apparatus comprises a closed loop member extending from a first side of the body portion to a second side of the body portion.

8. The housing of claim 1, wherein the support apparatus comprises a first support member and a second support member, wherein the first support member extends distally from the body portion and terminates in a first support pad, wherein the second support member extends distally from the body portion and terminates in a second support pad.

9. The housing of claim 8, wherein the first support pad further comprises an adhesive to adhere the first support pad to the support surface, wherein the second support pad further comprises an adhesive to adhere the second support pad to the support surface.

10. A fluid adjustment system comprising:
    (a) a needle system, wherein the needle system comprises a weight, wherein the needle system further comprises:
       (i) a needle, wherein the needle is configured to be inserted through an injection surface at an injection point,
       (ii) a needle accessory, wherein the needle accessory is in fluid communication with the needle, and
       (iii) a housing, wherein the housing is configured to engage the needle and the needle accessory, wherein the housing is further configured to provide fluid communication between the needle and the needle accessory; and
    (b) a support apparatus, wherein the support apparatus comprises:
       (i) a first end, wherein the first end is associated with the housing, and
       (ii) a second end, wherein the second end is configured to engage the injection surface at least one engagement point;
    wherein the support apparatus is configured to transfer at least a portion of the weight of the needle system to the at least one engagement point, wherein the at least one engagement point is spaced apart from the injection point.

11. The fluid adjustment system of claim 10, wherein the at least one engagement point is located above the injection point.

12. The fluid adjustment system of claim 10, wherein the at least one engagement point is located below the injection point.

13. The fluid adjustment system of claim 10, wherein the needle system further comprises a pressure sensor, wherein the pressure sensor is positioned within the housing.

14. The fluid adjustment system of claim 10, wherein the support apparatus is rotatably engaged with the housing via a spring-loaded hinge mechanism.

15. The fluid adjustment system of claim 10, wherein the needle accessory is selected from the group consisting of a syringe barrel and a piece of tubing.

16. A fluid adjustment system comprising:
    (a) a needle, wherein the needle is configured to be inserted through an injection surface into an implanted device;
    (b) a needle accessory, wherein the needle accessory is configured to be used in conjunction with the needle;
    (c) a pressure sensing component, wherein the pressure sensing component comprises:
       (i) a pressure sensor, wherein the pressure sensor is configured to measure the pressure associated with the implanted device, and
       (ii) a pressure sensor housing, wherein the pressure sensor housing is configured to contain the pressure sensor, wherein the pressure sensor housing is further configured to engage the needle, wherein the pressure sensor housing is further configured to engage the needle accessory; and
    (d) a stabilizer, wherein the stabilizer is engaged with the pressure sensor housing, wherein the stabilizer is configured to support the needle, the needle accessory, and the pressure sensing component.

17. The fluid adjustment system of claim 16, wherein the stabilizer comprises an arm extending from the pressure sensor housing.

18. The fluid adjustment system of claim 16 further comprising a cable, wherein the cable has a first end and a second end, wherein the first end is coupled with the pressure sensor housing, wherein the cable is configured to communicate data obtained by the pressure sensor to an external display, wherein the stabilizer comprises a weight coupled with the second end of the cable.

19. The fluid adjustment system of claim 18, wherein the cable comprises markings configured to provide measurement from the needle to a patient's xyphoid process.

* * * * *